Dec. 16, 1969 C. G. KLEHM Plant Pat. 2,954
PEONY
Filed May 22, 1968
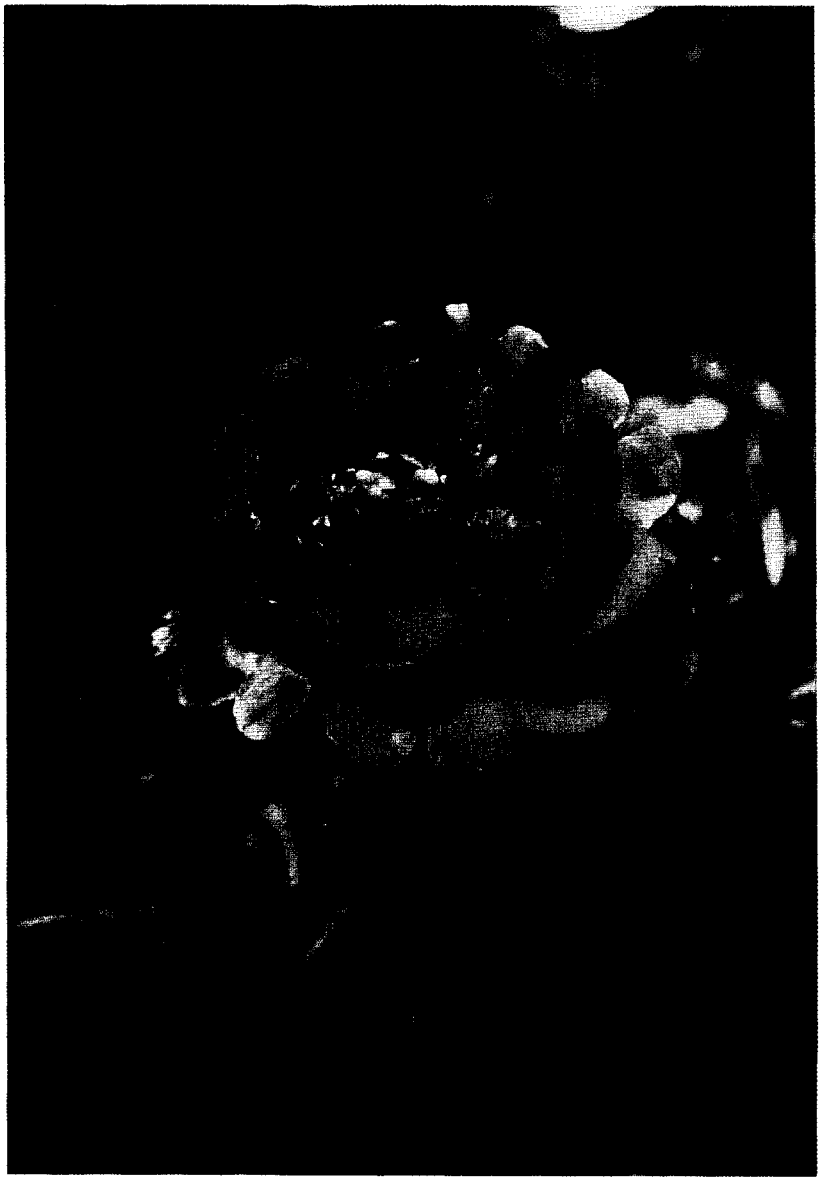
Inventor
Carl G. Klehm
By Hofgren, Wegner,
Allen, Stellman & McCord
Atty's United States Patent Office Plant Pat. 2,954
Patented Dec. 16, 1969

2,954
PEONY PLANT

Carl G. Klehm, 3 E. Algonquin Road,
Arlington Heights, Ill. 60005

Filed May 22, 1968, Ser. No. 731,343
Int. Cl. A01h 5/02
U.S. Cl. Plt.—68 1 Claim The present invention relates to a distinctly new variety of peony plant belonging to the genus Paeonia species *lactiflora*. It is especially new and distinct because of the color combination on its flower petals. A deep wine red and silver color combination makes the blossoms beautiful and unique. Its plant habit is stout and short with clean abundant foliage which especially qualifies this variety for garden and landscape use.

This peony plant was originated by me at my nursery in Arlington Heights, Ill., from a cross between David Harum, the seed parent, and Alice Harding, the pollen parent (both not patented). The process of hybridization was done by hand pollination and the mode of reproduction was asexual root division. Thousands of seedlings were developed as a result of this cross and from these thousands, this particular plant was selected for its unusual uniqueness. Since the original plant developed its first bloom, the variety has been under close observation in my nursery for eighteen (18) years under a variety of microclimatic conditions.

This peony plant derives its stout growth habit and abundant clean foliage from the pollen parent, Alice Harding. Its wine red color comes from the spectrum of red hues observed on blossoms of its seed parent, David Harum. The silver on the outer edges of the blossom petals comes from the hereditary traits of both parents.

The most unique quality of this variety is its flower color. From a distance, the blossoms are a deep wine red with dorsal silver highlights. Upon close examination, one finds that the base of the petals is the deepest of wine reds. This color gradually changes shades of red as the distance from the calyx increases until the petal edges become a beautiful silver. This unique silver color lines the upper outer edges of all the flower petals. Observation of blossoms from a distance gives a lake of silver effect while observation of a blossom from directly overhead gives a much more red influence. Another desirable characteristic of this variety is its stout plant growth habit. The stems are uniformly strong, short and stiff and hold the blossoms straight and erect. The foliage is even, full and lush.

The attractiveness of the blossoms, the weather resistant growth habit, and the clean, lush foliage all combine to make this variety desirable for home garden and landscape use.

The accompanying drawing shows a view of an individual flower, in color as nearly true as reasonably possible in a color illustration of this character.

As a convenient summary, the following detailed description of this new peony variety is given with color terminology generally in accordance with Kornerup and Wanscher's "Reinhold Color Atlas," 1961 edition, except where general color terms are used.

Parentage:

*Seed parent.*—David Harum, from which this variety obtains its deep red color and, combined with its pollen parent, its silver petal lining.

*Pollen parent.*—Alice Harding, from which this variety obtains its short, stout growth habit, abundant lush foliage and, combined with its seed parent, its silver petal lining.

FLOWER

Blooming habit: Annually.

Bud:

*Size.*—Medium large.
*Form.*—Smooth, round and even.
*Color.*—Deep red.
*Sepals.*—Smooth green wrapped tightly around bud.
*Calyx.*—Polysepalous.
*Peduncle.*—None.
*Opening.*—Unfailing opening qualities—a dependable annual performer.

Bloom:

*Size.*—Medium large—average size when fully opened 8–8½ inches.
*Borne.*—One main flower terminally borne with 0 to 4 axiallary smaller flowers.
*Form.*—Rose type with three to five rows of outer guard petals.
*Petalage.*—Medium double.
*Color.*—Predominant red 12B, 6 to 8—silver range 12B, 1–2.
*Variegations.*—None.
*Discolorations.*—None.

Petals:

*Texture.*—Medium thick but smooth.
*Appearance.*—Satiny inside and outside.
*Form.*—Not lanceolated.
*Arrangement.*—Double.
*Persistence.*—Drop off cleanly.
*Fragrance.*—Mild scent.
*Lastingness.*—On the plant, long.

Genital organs:

*Stamens, anthers.*—Yes, golden yellow.
*Stamens, filaments.*—⅜" to ⅝" long.
*Pollen.*—Yes.
*Styles.*—None.
*Stigmas.*—None.
*Ovaries.*—None.

Fruit: None.

PLANTS

Form: Herbaceous bush.
Growth: Uniform, strong.

Foliage:

*Leaflets.*—Five.
*Size.*—Medium large.
*Quantity.*—Above average.
*Color.*—Clean, lush green—the best of *lactiflora* species, extends from ground to bloom.
*Shape.*—Elliptically acute.
*Stem.*—Short, 26–28", average length—uniform.
*Texture.*—Pronounced vertical veins.
*Edge.*—Smooth.
*Serration.*—None.
*Leaf stem.*—Thick.
*Stipules.*—None.
*Disease resistance.*—Exceptionally resistant to fungus diseases which attack peonies. This was observed during the growing seasons of the last 18 years.

I claim:

1. A new and distinct variety of peony plant characterized by its unusual distinct color combination of the blossom and its complementary, unique growth habit.

No reference cited.

ROBERT E. BAGWILL, Primary Examiner